US012605323B2

(12) United States Patent
Choi et al.

(10) Patent No.: US 12,605,323 B2
(45) Date of Patent: **\*Apr. 21, 2026**

(54) COMPOSITION FOR INHIBITING HAIR GRAYING, AND USE THEREOF

(71) Applicant: LG HOUSEHOLD & HEALTH CARE LTD., Seoul (KR)

(72) Inventors: Yun-Ho Choi, Seoul (KR); Sanghwa Lee, Seoul (KR); Jae Young Shin, Seoul (KR); Jaeyoon Kim, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 626 days.

This patent is subject to a terminal disclaimer.

(21) Appl. No.: 18/000,034

(22) PCT Filed: May 28, 2020

(86) PCT No.: PCT/KR2020/006903
§ 371 (c)(1),
(2) Date: Nov. 28, 2022

(87) PCT Pub. No.: WO2021/241780
PCT Pub. Date: Dec. 2, 2021

(65) Prior Publication Data
US 2023/0201097 A1 Jun. 29, 2023

(51) Int. Cl.
| | |
|---|---|
| *A61K 8/60* | (2006.01) |
| *A61K 8/37* | (2006.01) |
| *A61K 8/46* | (2006.01) |
| *A61K 8/49* | (2006.01) |
| *A61K 8/63* | (2006.01) |
| *A61Q 5/06* | (2006.01) |

(52) U.S. Cl.
CPC ............... *A61K 8/604* (2013.01); *A61K 8/37* (2013.01); *A61K 8/46* (2013.01); *A61K 8/4973* (2013.01); *A61K 8/498* (2013.01); *A61K 8/63* (2013.01); *A61Q 5/065* (2013.01)

(58) Field of Classification Search
CPC . A61K 8/604; A61K 8/37; A61K 8/46; A61K 8/4973; A61K 8/498; A61K 8/63; A61Q 5/065
USPC .......................................................... 514/26
See application file for complete search history.

(56) References Cited

FOREIGN PATENT DOCUMENTS

| | | | |
|---|---|---|---|
| CN | 103830695 A | | 6/2014 |
| CN | 104825361 A | * | 8/2015 |
| CN | 106667858 A | | 5/2017 |
| CN | 109078054 A | | 12/2018 |
| JP | 2011-511063 A | | 4/2011 |
| KR | 10-2005-0105501 A | | 11/2005 |
| KR | 10-2015-0085671 A | | 7/2015 |
| KR | 10-2016-0029769 A | | 3/2016 |
| KR | 10-2018-0042706 A | | 4/2018 |
| KR | 10-2018-0045626 A | | 5/2018 |
| KR | 10-2063697 B1 | | 1/2020 |

OTHER PUBLICATIONS

Rabbani et al., "Coordinated Activation of Wnt in Epithelial and Melanocyte Stem Cells Initiates Pigmented Hair Regeneration", Cell, 2011, vol. 145, pp. 941-955, Jun. 10, 2011.

* cited by examiner

*Primary Examiner* — Yih-Horng Shiao
(74) *Attorney, Agent, or Firm* — Vorys, Sater, Seymour and Pease LLP; Mih Suhn Koh

(57) ABSTRACT

Provided is a composition for inhibiting hair graying, having an excellent effect of preventing the occurrence of gray hair, and a use thereof. A composition for inhibiting hair graying, of the presently claimed subject matter, activates the Wnt and β-catenin signaling pathway to promote melanin synthesis in hair, thereby having remarkably excellent hair graying (canities) inhibition, prevention, improvement, alleviation, delaying, or treatment effects.

3 Claims, 2 Drawing Sheets

INCREASE IN MELANIN SYNTHESIS CAUSED BY ESCIN

COMPOSITION FOR INHIBITING HAIR GRAYING, AND USE THEREOF

TECHNICAL FIELD

The present disclosure relates to a composition for inhibiting hair graying, which has an excellent effect of inhibiting development of gray hair, and use thereof.

BACKGROUND ART

Gray hair is developed as the aging of scalp proceeds. Hair graying includes canities and hair graying. Gray hair (white hair) makes the person who has it look older as compared to his/her actual age, depending on how severe it is. A change in hair color may be recognized as a signal of aging, and development of gray hair incompatible with age may function as stress to individuals and may adversely affect self-esteem. Therefore, various research and development have been conducted in order to improve hair graying cosmetically.

Even though hair dyeing is performed to improve hair graying, gray hair is grown continuously according to the growth of hair. Therefore, hair dyeing is disadvantageous in that its effect is temporary. As a result, hair dyeing is also disadvantageous in that periodical hair dyeing is required. In addition, conventional oxidative hair dyeing agents may cause damages on the scalp and skin. In addition, an extract of black beans or *Polygonum multiflorum* has been used to improve hair graying, but it is disadvantageous in that its effect is not enough to be felt.

Development of gray hair is mainly caused by loss of melanocyte stem cells (MSC) or degradation of physiological activity of melanocytes. Due to this, the amount of melanin produced in melanocytes present in hair, such as head hair, eyebrows or eyelashes, is reduced, resulting in progress of hair whitening or graying. Melanin produced in melanocytes is transferred to keratinocytes to form pigmented head hair or body hair. Herein, when melanin is not transferred to keratinocytes, deficiency of pigment in hair occurs, resulting in hair graying.

The amount and relative ratio of umelanins showing a brown color and black color and phenomelanins showing a yellow color and red color significantly affect the color of head hair and body hair. In addition, it is known that three types of enzymes of tyrosinase, DHICA oxidase (TRP-1) and DOPAchrome tautomerase (TRP-2) participate in production of melanin, and the activity of the enzymes affects melanin synthesis. In this process, tyrosinase catalyzes oxidation of tyrosine into DOPA and oxidation of DOPA into dopaquinone. The material known as L-dopaquinone or o-dopaquinone is a melanin precursor. Dopaquinone is naturally undergoes cyclization in the presence of cysteine and is converted into dopachrome, which, in turn, is tautomerized by DOPAchrome tautomerase (TRP-2) to form DHICA. TRP-1 oxidizes DHICA to form a quinone derivative.

Among the enzymes, tyrosinase and TRP-1 are developed melanocytes around the hair bulb and dermal papilla during the anagen in the hair follicle growth cycle, and are not developed during the catagen and telogen.

As mentioned above, hair graying is affected by both melanocytes and melanocyte stem cells. In addition, when melanin cells are reduced, formation of melanin is gradually reduced accordingly and transfer of melanin is decreased. Such a decrease in melanin may appear in the form of a pigmented disease. A typical example of pigmented disease is vitiligo, and one of the causes of vitiligo is a decrease or destruction of melanocytes. In addition, as a method for treating vitiligo, activation of the Wnt/β-catenin signaling pathway has been studied intensively (Journal of Investigative Dermatology (2015) 135, 2921-2923). Further, it is reported that when the Wnt signaling mechanism of melanocyte stem cells is activated, pigment formation is increased in hair and epidermal melanocytes (Cell, Vol 145, Issue 6, 10, (2011), 941-955) (Medical Research Review (2016), Vol 37, issue 4, 907-945).

DISCLOSURE

Technical Problem

The present disclosure is designed to solve the problems of the related art, and therefore the present disclosure is directed to providing a composition for inhibiting hair graying which can effectively inhibit/suppress development of gray hair.

The present disclosure is also directed to providing use of the composition in a method of inhibiting/suppressing development of gray hair.

Technical Solution

The inventors of the present disclosure have conducted intensive studies in order to discover a material capable of inhibiting/suppressing hair graying including canities effectively and have found that escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII or platycodin D2 activates the Wnt/β-catenin signaling pathway. The inventors have also found that the above-mentioned ingredients have an effect of enhancing melanin synthesis in B-16 mouse melanoma cells. The inventors of the present disclosure have found that when at least one of the above-mentioned ingredients having an excellent effect of activating the Wnt/β-catenin signaling pathway is applied (spread) to the skin, it is possible to obtain a significantly high effect of inhibiting or suppressing or improving hair graying. The present disclosure is based on this finding.

In one aspect of the present disclosure, there is provided a composition for inhibiting/suppressing hair graying including at least one selected from the group consisting of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2. The composition for inhibiting/suppressing hair graying may include at least one the above-mentioned ingredients as an active ingredient.

According to the present disclosure, 'inhibiting/suppressing hair graying' may refer to 'inhibiting or suppressing the amount or frequency of development of gray hair' or 'inhibiting or suppressing a process including a change or aging from black hair into gray hair'. According to an embodiment, 'inhibiting or suppressing hair graying' may refer to activation of the Wnt/β-catenin signaling pathway, resulting in acceleration of melanin synthesis in hair. According to an embodiment, the composition for inhibiting hair graying according to the present disclosure may be used for inhibiting, suppressing, preventing, improving, alleviating, delaying or treating hair graying (canities), and may be used for any application with no particular limitation, as long as it is used for the cosmetic purpose in order to improve hair graying. The term 'prevent' may cover any action of delaying the progress of development, growth or proliferation of gray hair by using the composition according to the present disclosure. The term 'treat' may cover any action of inhibiting growth and proliferation of gray hair by using the composition according to the present disclosure to induce improvement or a positive change in hair graying or canities.

According to an embodiment, the composition for inhibiting hair graying according to the present disclosure may include at least one selected from the group consisting of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2, in an amount of 0.0001-50 wt %, preferably 0.001-10 wt %, based on the total weight of the composition. When the content of the active ingredient is less than 0.0001 wt %, it is not possible to obtain a sufficient effect of inhibiting hair graying. When the content of the active ingredient is larger than 50 wt %, formulation stability may be degraded undesirably.

According to an embodiment, the composition for inhibiting hair graying according to the present disclosure may be used as a pharmaceutical composition, a quasi-drug composition or a cosmetic composition. In addition, the composition for inhibiting hair graying according to the present disclosure may be formulated into any formulation generally applicable to the skin. Preferably, the composition for inhibiting hair graying according to the present disclosure may be formulated into a formulation for external use on the skin. For example, the formulation for external use on the skin may be prepared as a formulation applicable to the skin, such as liquid, cream, paste or solid. In addition, the composition for inhibiting hair graying according to the present disclosure may be provided as a composition or product for use in hair or scalp, and for example, it may be prepared in the form a composition, such as shampoo, tonic, hair conditioner, hair lotion, gel, pack, cream, essence, powder, spray, oil, soap, liquid cleaner, liquid hair dyeing agent or aerosol for inhibiting hair graying, by adding conventional additives thereto, but is not limited thereto. In the following Preparation Examples 1 or 2 according to the present disclosure, the composition for inhibiting hair graying is prepared in a hair tonic or hair lotion formulation.

According to an embodiment, when the composition for inhibiting hair graying according to the present disclosure is liquid, a solvent, a solvating agent or an emulsifier may be used as a carrier ingredient. For example, the carrier ingredient may include at least one selected from the group consisting of water, alcohol, ethyl carbonate, ethyl acetate, benzyl alcohol, benzyl benzoate, propylene glycol, 1,3-butylglycol oil, glycerol fatty acid ester, polyethylene glycol, and sorbitan fatty acid ester. The alcohol may be any alcohol used conventionally, preferably a linear or branched C2-C4 monoalcohol, and more preferably, ethanol or isopropanol, but is not limited thereto.

According to an embodiment, when the composition for inhibiting hair graying according to the present disclosure is paste, cream or gel, animal oil, vegetable oil, wax, paraffin, starch, tragacanth, cellulose derivative, polyethylene glycol, silicone, bentonite, silica, talc or zinc oxide may be used as a carrier ingredient. In addition, alcohol may be used as a carrier ingredient. Preferably, the alcohol may include isopropanol, but is not limited thereto.

According to an embodiment, when the composition for inhibiting hair graying according to the present disclosure is powder or spray, lactose, talc, silica, aluminum hydroxide, calcium silicate or polyamide powder may be used as a carrier ingredient. When the formulation is spray, a propellent, such as chlorofluorohydrocarbon, propane/butane or dimethyl ether, may be further used.

According to an embodiment, the composition for inhibiting hair graying according to the present disclosure may include ingredients that may be used conventionally in a formulation for external use on the skin. For example, the composition may further include at least one additive selected from the group consisting of water, surfactant, moisturizing agent, lower alcohol, chelating agent, sterilizing agent, antioxidant, preservative, pigment and fragrance.

According to an embodiment, the composition for inhibiting hair graying according to the present disclosure may be used through a transdermal administration route, for example, by applying or spraying it directly onto the skin. The term 'administration' means introduction of the composition for inhibiting hair graying according to the present disclosure to the body through any suitable method. The administration route of the composition for inhibiting hair graying according to the present disclosure may be conventional route, as long as it allows delivery of the composition to a target tissue. Preferably, the composition for inhibiting hair graying according to the present disclosure may be administered through a transdermal route, and more preferably, may be locally administered. The number of application of the composition for inhibiting hair graying according to the present disclosure may be determined depending on the prescription, need or purpose.

According to an embodiment, the dose of the composition for inhibiting hair graying according to the present disclosure may be controlled suitably depending on personal characteristics, such as age or lesion severity, or formulation. In addition, the composition for inhibiting hair graying according to the present disclosure may be used preferably by applying it in an adequate amount to the scalp once or several times per day for 1 week to several months. In the following Test Example 3 according to the present disclosure, a composition (hair tonic) for inhibiting hair graying is used for 6 months, seven times per week. As can be seen from the result of Test Example 3, the hair tonic provides a higher effect of inhibiting hair graying as compared to the placebo control according to Comparative Example. Particularly, a formulation including ethanol shows an even higher effect of preventing hair loss and improving hair growth.

In another aspect of the present disclosure, there is provided a kit for inhibiting hair graying, including the composition for inhibiting hair graying according to the present disclosure. The kit refers to a set including a composition required for preventing or treating hair graying and accessories. According to an embodiment, the accessories contained in the kit include tools or instruments used conventionally in the art for preventing or treating hair graying. According to another embodiment, the kit may further include administration instruction in which at least one information selected from the group consisting of the administration dose, route and number and applicable conditions (canities) is described.

In still another aspect of the present disclosure, there is provided a method for inhibiting hair graying, including applying the composition for inhibiting hair graying according to the present disclosure to a subject in need thereof. According to an embodiment, the subject may be a human in need of inhibition of hair graying. Preferably, the method may include applying an effective dose of the composition for inhibiting hair graying to a subject. The term 'effective dose' means the amount of the active ingredient sufficient to inhibit, delay, improve or alleviate hair graying, or to provide a therapeutic or cosmetic advantage in treating or managing hair graying. In addition, the term 'effective dose' means the amount of the active ingredient sufficient to inhibit or reduce development of gray hair in vitro or in vivo. The method for inhibiting hair graying can activate the Wnt/β-catenin signaling pathway and accelerate melanin synthesis in hair, thereby providing an effect of inhibiting or improving hair graying.

In still another aspect of the present disclosure, there is provide use of the composition for inhibiting hair graying in applications for inhibiting hair graying. According to an embodiment, the use may include any use for inhibiting or improving hair graying. For example, the use may include pharmaceutical use, cosmetic use or cosmetologic use. According to another embodiment, the use for inhibiting hair graying can activate the Wnt/β-catenin signaling pathway and accelerate melanin synthesis in hair, thereby providing an effect of inhibiting or improving hair graying.

In yet another aspect of the present disclosure, there is provided a method for preparing a composition for inhibiting hair graying including at least one selected from the group consisting of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2. In the method, the composition for inhibiting hair graying may be prepared by any conventional method for preparing a cosmetic product, a quasi-drug or a pharmaceutical product.

According to an embodiment, the composition for inhibiting hair graying according to the present disclosure may include two or more ingredients selected from the group consisting of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2.

According to an embodiment, the composition for inhibiting hair graying according to the present disclosure does not contain all ingredients disclosed herein in excess of the maximum amount of use prescribed by the various norms related with cosmetics/foods/medicines/quasi-drugs.

Advantageous Effects

The composition for inhibiting hair graying according to the present disclosure can inhibit development of gray hair effectively. The composition for inhibiting hair graying according to the present disclosure can activate the Wnt/β-catenin signaling pathway and accelerate melanin synthesis in hair, thereby providing a significantly high effect of inhibiting, preventing, improving, alleviating, delaying or treating hair graying (canities).

BEST MODE

Figure 1:
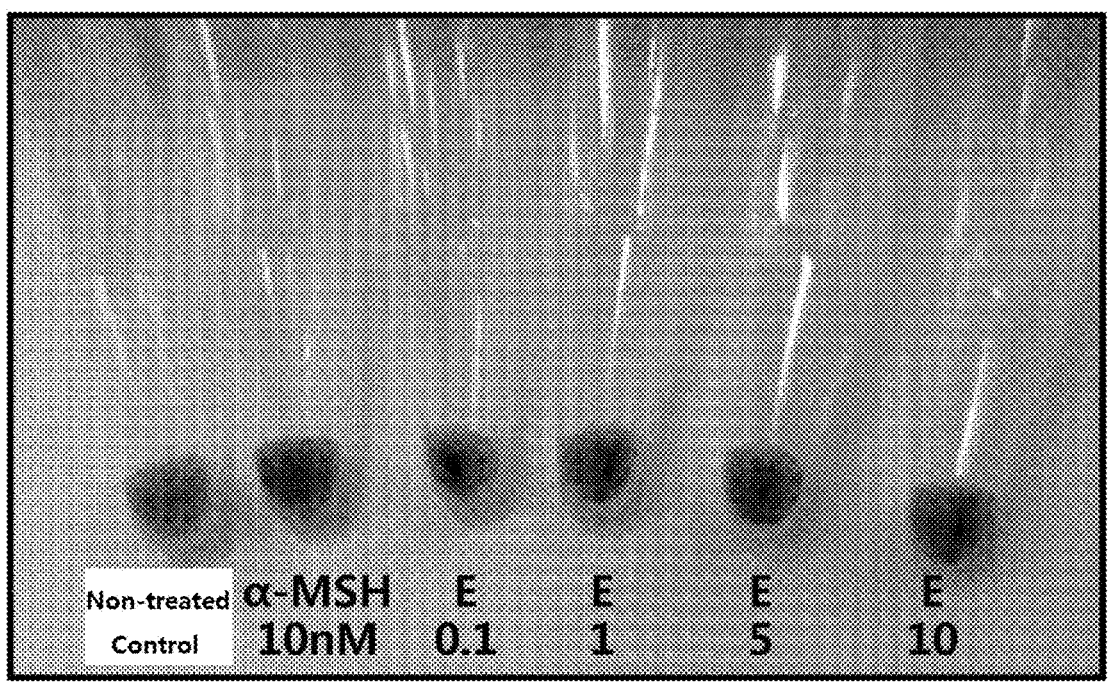
FIG. 1 shows the test result illustrating an increase in melanin synthesis caused by escin in B-16 melanoma cells.

Examples will be described more fully hereinafter so that the present disclosure can be understood with ease. The following examples may, however, be embodied in many different forms and should not be construed as limited to the exemplary embodiments set forth therein.

Rather, these exemplary embodiments are provided so that the present disclosure will be thorough and complete, and will fully convey the scope of the present disclosure to those skilled in the art.

Test Example 1: Effect of Enhancing Wnt/β-Catenin Signaling

To determine activation of the Wnt/β-catenin signaling pathway, TCF/LEF Responsive Luciferase Reporter HEK293A stabilized cell line (Wnt Reporter HEK293A cell; WRHEK293A) was used in this test. The stabilized cell line was maintained through the subculture using MEM (Corning, USA) and fetal bovine serum (Gibco BRL, Gaithersburg, MD, USA). To carry out a transcriptional activity test, 30,000 cells were seeded per well in a 96-well plate and cultured in an incubator at 37° C. for 24 hours. Then, according to the present disclosure, treatment with each of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2 was carried out as shown in the following Table 1. After culturing for 24 hours, a luciferase assay system (Promega) was used to perform reporter analysis. The analysis was carried out by the test method provided by the production company, and luminescence was determined by using Victor multiwall plate reader (PerkinElmer, USA). To determine cytotoxicity caused by the treatment, development of fluorescence of GFP as an internal control was determined. The luminescence value derived from the reaction with luciferase was divided by the GFP fluorescence value, and the values of the test group were calculated by taking the value of the non-treated control as 100% and expressed in the unit of percentage (%) (Table 1).

TABLE 1

Effect of Enhancing Wnt/β-Catenin Signaling

| Concentration (μg/mL) | | Wnt signaling activation capability (%) (Luminescence/GFP) |
|---|---|---|
| Non-treated control | | 100 |
| Escin | 10 | 1098 |
| 27-Deoxyactein | 10 | 1717 |
| Lysionotin | 10 | 196 |
| Nitidine chloride | 10 | 274 |
| Lanosterol | 10 | 194 |
| Engeletin | 10 | 223 |
| Specnuezhenide | 10 | 243 |
| Praeruptorin B | 10 | 241 |
| Rotunic acid | 10 | 296 |
| Sesamoside | 10 | 275 |
| Polygalacin D | 10 | 292 |
| Momordin Ic | 10 | 370 |
| Valechlorine | 10 | 218 |
| Tussilagone | 10 | 195 |
| Periplocin | 10 | 244 |
| Polyphyllin VII | 10 | 275 |
| Platycodin D2 | 10 | 216 |

Test Example 2: Determination of Effect of Producing Melanin

In this test, the compounds in Test Example 1 showing an effect of enhancing the Wnt signaling were added to the culture medium of mouse-derived melanoma cells (B-16 mouse melanoma cells) to determine the effect of producing melanin in a cellular level (Lotan R., Lotan D. Cancer Res. 40: 3345-3350, 1980). Before the test, B-16 melanoma cells were evaluated in terms of toxicity, and the non-toxic concentration was selected to carry out evaluation of melanin production. B-16 melanoma cells were subcultured in DMEM (Gibco BRL., Gaithersburg, MD, USA) containing 10% FBS. Then, seeding to a 100 mm cell culture dish was performed to synthesize and extract melanin, and the cells were treated with each compound when the confluency was 70%. The compound was used for treating the cell culture at a concentration of 10 μg/mL. In addition, α-melanocyte stimulating hormone (α-MSH) was used as control, added to the culture medium to 10 nM to treat B-16 melanoma cells, and cultured for 48 hours. Then, the cells were treated with trypsin to strip them off the culture container, and centrifugal separation was carried out to extract melanin. After that, 1 mL of sodium hydroxide (1 N concentration) solution was added to the stripped cells and the mixture was boiled for 10 minutes so that melanin may be dissolved. The amount of melanin production was determined by measuring the absorbance at 400 nM by using a spectrophotometer. The amount of melanin was quantified in the unit of μg/mL by using a standard absorbance curve as a function of melanin concentration. The value of the non-treated control was taken as 100%, and the values of the test group were calculated as a percentage (%) on the basis thereof (Table 2).

TABLE 2

Melanin Synthesis

| Concentration (μg/mL) | | Melanin synthesis (%) |
| --- | --- | --- |
| Non-treated control | | 100 |
| α-MSH (10 nM) | | 135 |
| Escin | 10 | 154 |
| 27-Deoxyactein | 10 | 168 |
| Lysionotin | 10 | 135 |
| Nitidine chloride | 10 | 125 |
| Lanosterol | 10 | 110 |
| Engeletin | 10 | 121 |
| Specnuezhenide | 10 | 106 |

TABLE 2-continued

Melanin Synthesis

| Concentration (μg/mL) | | Melanin synthesis (%) |
| --- | --- | --- |
| Praeruptorin B | 10 | 136 |
| Rotunic acid | 10 | 144 |
| Sesamoside | 10 | 112 |
| Polygalacin D | 10 | 114 |
| Momordin Ic | 10 | 131 |
| Valechlorine | 10 | 139 |
| Tussilagone | 10 | 136 |
| Periplocin | 10 | 128 |
| Polyphyllin VII | 10 | 127 |
| Platycodin D2 | 10 | 119 |

Figure 2:
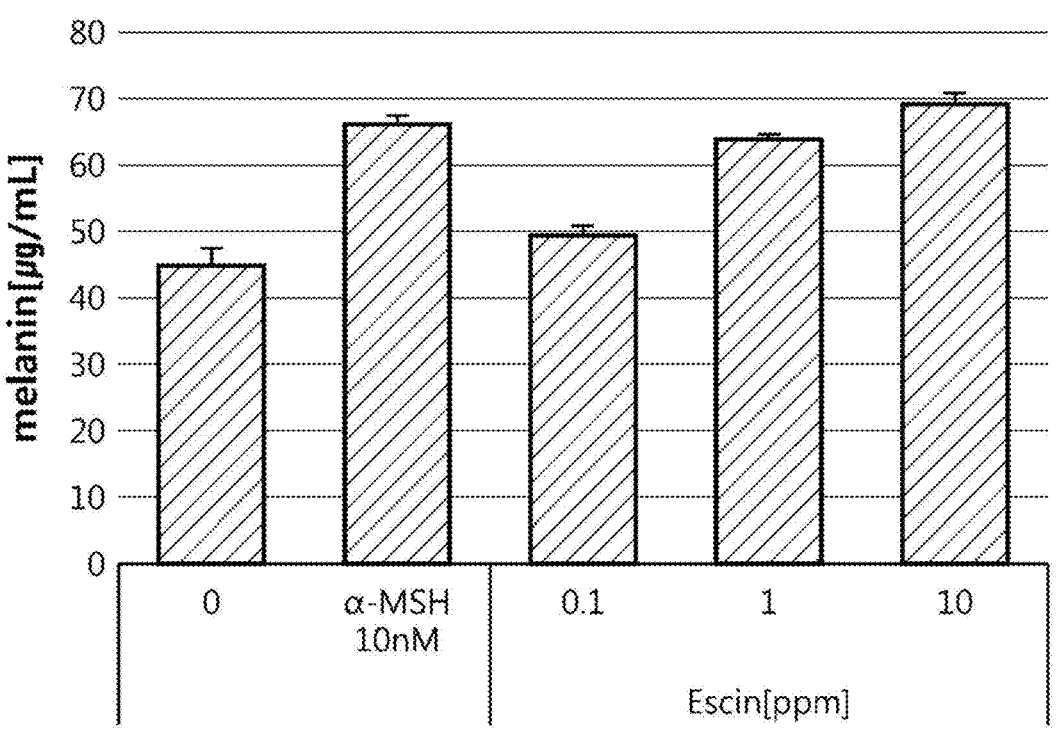
FIG. 2 is a graph illustrating an increase in melanin synthesis depending on escin and content thereof.

Among the compounds, the result of melanin synthesis derived from escin are shown in FIG. 1 and FIG. 2.

Test Example 3: Test for Determining Effect of Inhibiting Development of Gray Hair of Composition 1 (Hair Tonic) for Inhibiting Hair Graying Composition 1 (hair tonic) including escin and 27-deoxy-actein among the compounds according to the present disclosure for inhibiting hair graying was prepared. The composition was used to test the effect of reducing hair graying in the human hair. Herein, 60 healthy adults having gray hair participated in the test as subjects and were divided into five groups each including 12 subjects, and each test subject was allowed to use each of Comparative Example 1, Example 1, Example 1-2, Example 2 and Example 2-2 on his/her scalp for 6 months, 7 times per week. After the use, Folliscope phototrichogram was used to evaluate a degree of gray hair development as compared to the hair before applying the composition. The test result was expressed in the unit of percentage based on the value before application taken as 100%. The results are shown in Table 3.

TABLE 3

| | | Degree of gray hair development | | | | |
| --- | --- | --- | --- | --- | --- | --- |
| Sample | | Application start | After 4 weeks | After 8 weeks | After 12 weeks | After 24 weeks |
| Comp. Ex. 1 | Placebo control | 100 ± 3% | 105 ± 5% | 109 ± 4% | 119 ± 4% | 125 ± 6% |
| Ex. 1 | Escin 1% | 100 ± 4% | 104 ± 3% | 105 ± 5% | 107 ± 4% | 107 ± 4% |
| Ex. 1-2 | Escin 1% free from ethanol | 100 ± 4% | 104 ± 2% | 107 ± 4% | 110 ± 4% | 113 ± 5% |
| Ex. 2 | 27-Deoxyactein 1% | 100 ± 3% | 106 ± 2% | 108 ± 2% | 110 ± 7% | 110 ± 6% |
| Ex. 2-2 | 27-Deoxyactein 1% free from ethanol | 100 ± 3% | 105 ± 2% | 108 ± 3% | 113 ± 4% | 115 ± 5% |

Preparation Example 1: Composition 1 for Inhibiting Hair Graying (Hair Tonic)

According to the present disclosure, each of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2 was used to prepare hair tonic by using the conventional method according to the formulations as shown in the following Table 4.

TABLE 4

| | Ingredients | Ethanol | Castor oil | Glycerin | Active ingredient | | Fragrance and pigment | Purified water |
|---|---|---|---|---|---|---|---|---|
| Weight ratio (%) | Comp. Ex. 1 | 55 | 5 | 3 | 0 | | q.s. | Balance (total 100%) |
| | Ex. 1 | 55 | 5 | 3 | Escin | 1 | q.s. | |
| | Ex. 1-2 | 0 | 5 | 3 | Escin | 1 | q.s. | |
| | Ex. 2 | 55 | 5 | 3 | 27-Deoxyactcin | 1 | q.s. | |
| | Ex. 2-2 | 0 | 5 | 3 | 27-Deoxyactcin | 1 | q.s. | |
| | Ex. 3 | 55 | 5 | 3 | Lysionotin | 1 | q.s. | |
| | Ex. 4 | 55 | 5 | 3 | Nitidine chloride | 1 | q.s. | |
| | Ex. 5 | 55 | 5 | 3 | Lanosterol | 1 | q.s. | |
| | Ex. 6 | 55 | 5 | 3 | Engeletin | 1 | q.s. | |
| | Ex. 7 | 55 | 5 | 3 | Specnuezhenide | 1 | q.s. | |
| | Ex. 8 | 55 | 5 | 3 | Praeruptorin B | 1 | q.s. | |
| | Ex. 9 | 55 | 5 | 3 | Rotunic acid | 1 | q.s. | |
| | Ex. 10 | 55 | 5 | 3 | Sesamoside | 1 | q.s. | |
| | Ex. 11 | 55 | 5 | 3 | Polygalacin D | 1 | q.s. | |
| | Ex. 12 | 55 | 5 | 3 | Momordin Ic | 1 | q.s. | |
| | Ex. 13 | 55 | 5 | 3 | Valechlorine | 1 | q.s. | |
| | Ex. 14 | 55 | 5 | 3 | Tussilagone | 1 | q.s. | |
| | Ex. 15 | 55 | 5 | 3 | Periplocin | 1 | q.s. | |
| | Ex. 16 | 55 | 5 | 3 | Polyphyllin VII | 1 | q.s. | |
| | Ex. 17 | 55 | 5 | 3 | Platycodin D2 | 1 | q.s. | |

Preparation Example 2: Composition 2 for Inhibiting Hair Graying (Hair Lotion)

According to the present disclosure, each of escin, 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2 was used to prepare hair lotion by using the conventional method according to the formulations as shown in the following Table 5.

TABLE 5

| Ingredients | Weight ratio (%) |
|---|---|
| Cetostearyl alcohol | 2 |
| Stearyltriethylammonium chloride | 2 |
| Hydroxyethyl cellulose | 0.5 |
| At least one of Escin, 27-Deoxyactein, Lysionotin, Nitidine chloride, Lanosterol, Engeletin, Specnuezhenide, Praeruptorin B, Rotunic acid, Sesamoside, Polygalacin D, Momordin Ic, Valechlorine, Tussilagone, Periplocin, Polyphyllin VII and Platycodin D2 | 0.01 |
| Fragrance and pigment | q.s. |
| Purified water | Balance (total 100%) |

What is claimed is:

1. A method for suppressing hair graying, in a subject in need thereof, comprising applying to the subject a composition comprising at least one active ingredient selected from the group consisting of 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2 in an effective amount to activate the Wnt/β-catenin signaling system to promote melanic synthesis in hair, and thereby suppressing hair graying in the subject.

2. A method for suppressing hair graying in a subject in need thereof, comprising applying to the subject a composition consisting of: (i) an effective amount of escin to activate the Wnt/β-catenin signaling system to promote melanic synthesis in hair for suppressing hair graying; and (ii) a conventional carrier or additive for formulating the composition, and thereby suppressing hair graying in the subject.

3. A method for suppressing hair graying in a subject in need thereof, comprising applying to the subject a composition consisting of: (i) an effective amount of escin to activate the Wnt/β-catenin signaling system to promote melanic synthesis in hair for suppressing hair graying in combination with at least one of 27-deoxyactein, lysionotin, nitidine chloride, lanosterol, engeletin, specnuezhenide, praeruptorin B, rotundic acid, sesamoside, polygalacin D, momordin Ic, valechlorine, tussilagone, periplocin, polyphyllin VII and platycodin D2, and (ii) a conventional carrier or additive for formulating the composition, and thereby suppressing hair graying in the subject.

\* \* \* \* \*